United States Patent [19]

Wall et al.

[11] Patent Number: 5,227,380

[45] Date of Patent: * Jul. 13, 1993

[54] PHARMACEUTICAL COMPOSITIONS AND METHODS EMPLOYING CAMPTOTHECINS

[75] Inventors: Monroe E. Wall, Chapel Hill; Mansukh C. Wani, Durham; Allan W. Nicholas; Govindarajan Manikumar, both of Raleigh, all of N.C.

[73] Assignee: Research Triangle Institute, Research Triangle Park, N.C.

[ * ] Notice: The portion of the term of this patent subsequent to Jan. 16, 2007 has been disclaimed.

[21] Appl. No.: 636,150

[22] Filed: Dec. 31, 1990

Related U.S. Application Data

[63] Continuation of Ser. No. 250,094, Sep. 28, 1988, Pat. No. 4,981,968, which is a continuation-in-part of Ser. No. 32,449, Mar. 31, 1987, Pat. No. 4,894,456.

[51] Int. Cl.$^5$ .................. A61K 31/47; C07D 491/147; C07D 491/22
[52] U.S. Cl. .................. 514/253; 514/283; 544/361; 546/41; 546/48
[58] Field of Search .......... 546/41, 48; 544/361; 514/253, 283

[56] References Cited

U.S. PATENT DOCUMENTS

| | | | |
|---|---|---|---|
| 4,031,098 | 6/1977 | Sugasawa | 546/48 |
| 4,473,692 | 9/1984 | Miyasaka et al. | 546/48 |
| 4,545,880 | 10/1985 | Miyasaka et al. | 546/48 X |
| 4,604,463 | 8/1986 | Miyasaka et al. | 544/125 |
| 4,894,456 | 1/1990 | Wall et al. | 546/41 |
| 4,914,205 | 4/1990 | Sawada et al. | 546/70 |
| 4,981,968 | 1/1991 | Wall et al. | 544/361 |

FOREIGN PATENT DOCUMENTS

| | | |
|---|---|---|
| 00743256 | 3/1983 | European Pat. Off. . |
| 321122 | 6/1989 | European Pat. Off. . |
| 82116015 | 7/1982 | Japan . |
| 59-05188 | 1/1984 | Japan . |
| 59-46284 | 3/1984 | Japan . |
| 59-51287 | 3/1984 | Japan . |
| 59-51289 | 3/1984 | Japan . |
| 6185389 | 4/1984 | Japan . |
| 61-50985 | 3/1986 | Japan . |
| 61-85319 | 4/1986 | Japan . |

OTHER PUBLICATIONS

*Cancer Research*, (1989), vol. 49, 4385–5489, "DNA Topoisomerase I–Meditated DNA Cleavage and Cytotixicity of Camptothecin Analogues", Hisang et al.

*Cancer Research*, (1989) vol. 49, 1465–1469, "Structure-Activity Study of the Actions of Camptothecin Derivatives on Mammalian Topoisomerase I . . . " Jaxel et al.

*The Journal of Biological Chemistry*, (1985, 260, 14873–14878, "Camptothecin Induces Protein-Linked DNA Breaks via Mammalian DNA Topoisomerase I" Hsiang et al.

*J. Med. Chem.*, (1980), 23, 544–560, "Plant Antitumor Agents. 18.[1] Synthesis and Bilogical Activity of Camptothecin Analogues", Wani et al.

*J. Med. Chem.*, (1986), 29, 1553–1555, "Plant Antitumor Agents 22.[1] Isolation of 11-Hydroxycamptothecin From *Camptotheca acuminata* Decne . . . " Wall et al.

*Journal of Labelled Compounds and Radiopharmaceuticals*, (1981), 18, 319–329, "The Preparation of Tritium and Deuterium-Labelled Camptothecin", Ronman et al.

*J. Medicinal Chemistry*, (1987), 30, 1774–1779, "Plant Antitumor Agents 25.[1] Total Synthesis and Antileukemic Activity of Ring A . . . ", Wani et al.

(List continued on next page.)

*Primary Examiner*—Diana Rivers
*Attorney, Agent, or Firm*—Oblon, Spivak, McClelland, Maier & Neustadt

[57] ABSTRACT

A method for synthesizing camptothecin and camptothecin analogs using a novel hydroxyl-containing tricyclic intermediate and the camptothecin analogs produced by the process. The camptothecin analogs are effective inhibitors of topoisomerase I and show antileukemic and anti-tumor activity.

13 Claims, 3 Drawing Sheets

OTHER PUBLICATIONS

*J. Medicinal Chemistry*, (1990), 33, 972-978, "Plant Antitumor Agents. 29.[1] Synthesis and Biological Activity of Ring D and Ring 3 . . . " Nicholas et al.

*J. Org. Chem.* (1974), 39, 303-311, "Synthesis of Some DE and CDE Ring Analogs of Camptothecin", Plattner et al.

*J. of Am. Chem. Soc.* (1972), 94, 8615, "Synthesis of Some DE and CDE Ring Analogs of Camptothecin" Plattner et al.

*J. Org. Chem.*, (1974), 39, 3430-3432, "Synthesis of Biological Evaluation of De-AB-Camptothecin", Danishefsky et al.

Govindachari et al., "9-Methoxycamptothecin. A New Alkaloid from Mappia Foetida Miers" Indian J. Chem. vol. 10 (4) 453-454 (1972).

*Proc. Annu. Meet. Am Assoc. Cancer Res.*, (1988), 29, A1080, "Structure-Activity Study of the Relation Between Topoisomerase I Inhibition and Antitumor . . . " Abstract.

*Proc. Annu. Meet. Am Assoc. Cancer Res*, (1989), 8, A1019, "A Clinical Study of A Camptothecin Derivative, CPT-11 on Hematological Malignancies", (Mtg Abstract).

*Proc. Ann. Meet. Am Assoc. Cancer Res*, (1989), 30, A2485, "Irreversible Trapping of the DNA-Topoisomerase I Covalent Complex and Affinity Labeling of . . . " Mtg Abstract.

*J. Med. Chem*, (1989), 32, 715-720, "Modification of the Hydroxy Lactone Ring of Camptothecin: Inhibition of Mammalian Topoisomerase I and . . . ", Mong et al. Abstract.

*Science*, (1989), 246, 1046-1048, "DNA Topoisomerase I-Targeted Chemotherapy of Human Colon Cancer in Xenografts", Giovanella et al.

*Proc. Annu. Meet. Am. Assoc. Cancer Res.*, (1989), A2476, "Structure-Activity Studies of 20(S)-Captothecin Analogs" (Meeting Abstract).

Yang, et al. (AR13), Chemical Abstracts, vol. 100: 139434w (1984).

Pan, et al. (AR14), Chemical Abstracts, vol. 84: 115629p (1976).

PHARMACEUTICAL COMPOSITIONS AND METHODS EMPLOYING CAMPTOTHECINS

This is a continuation of application Ser. No. 07/250,094, filed on Sep. 28, 1988, now U.S. Pat. No. 4,981,968 which is a continuation-in-part of Ser. No. 07/032,449, filed on Mar. 31, 1987, now U.S. Pat. No. 4,894,456.

BACKGROUND OF THE INVENTION

1. Field of the Invention

The invention relates to camptothecin and analogs thereof which show life prologation effects in various leukemia systems such as P-388 and L-1210; inhibition of animal tumors such as B-16 melanoma and are potent inhibitors of topoisomerases I and II. It also relates to a method of synthesizing the same by means of a novel hydroxyl-containing tricyclic intermediate.

2. Discussion of the Background

Camptothecin is a pentacyclic alkaloid initially isolated from the wood and bark of Camptotheca acuminata by Wall et al (M.E. Wall, M.C. Wani, C.E. Cook, K.H. Palmer, A.T. McPhail, and G.A. Sim, *J. Am. Chem. Soc.*, 94, 388 (1966).

Camptothecin is highly biologically active and displays strong inhibitory activity toward the biosynthesis of nucleic acids. Additionally, camptothecin exhibits potent anti-tumor activity against experimentally transplanted carcinoma such as leukemia L-1210 in mice or Walker 256 tumor in rats.

Several methods for the synthesis of camptothecin and camptothecin analogs are known. These synthetic methods include (i) methods in which naturally occurring camptothecin is synthetically modified to produce a number of analogs and (ii) totally synthetic methods.

U.S. Pat. Nos. 4,604,463; 4,545,880; and 4,473,692 as well as European Patent Application 0074256 are examples of the former type of synthetic strategy. Additional examples of this strategy can be found in Japanese Patents 84/46,284; 84/51,287; and 82/116,015. These methods required naturally occurring camptothecin which is difficult to isolate and hence these methods are not suitable for the production of large quantities of camptothecin or analogs.

Examples of a variety of totally synthetic routes to camptothecin and camptothecin analogs can be found in the following references: *Sci. Sin. (Engl. Ed)*, 21(1), 87–98 (1978); *Fitoterpapia*, 45(3), 87–101 (1974); *Yakugaku Zashi*, 92(6), 743-6 (1972); *J. Org. Chem.*, 40(14), 2140-1 (1975); *Hua Hsueh Hsueh Pao*, 39(2), 171-8 (1981); *J. Chem. Soc., Perkin Trans* 1, (5), 1563-8 (1981); *Heterocycles*, 14(7), 951-3 (1980); *J. Amer. Chem. Soc.*, 94(10), 3631-2 (1972); *J. Chem. Soc. D*, (7), 404 (1970) and U.S. Pat. No. 4,031,098.

Wani et al, *J. Med. Chem.*, 23, 554 (1980) discloses a synthesis of camptothecin and camptothecin analogs which involves the reaction of a tricyclic compound with a suitably substituted orthoaminoaldehyde to yield desoxycamptothecin as shown in Equation 1 below.

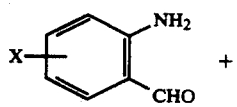
+
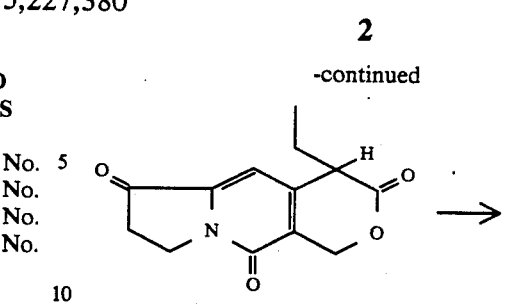

(Equation 1)

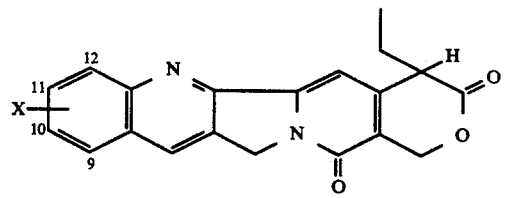

Desoxycamptothecin is then treated with oxygen to give camptothecin analogs. A major disadvantage of this procedure is the insolubility of desoxycamptothecin and its analogs, requiring large solvent volumes in the final step. A poor yield of the oxygenation product results under these conditions.

There exists a need, therefore, for a high-yield, efficient synthesis of camptothecin and camptothecin analogs which does not require prior isolation of naturally occurring camptothecin.

A need also exists for a method of synthesizing camptothecin and camptothecin analogs which does not suffer from insolubility problems of intermediate compounds and the resulting low yields.

A further need exists for new camptothecin analogs which can be synthesized in an efficient, high-yield manner and which show good biological activity.

SUMMARY OF THE INVENTION

Accordingly, one object of the present invention is to provide a method of synthesizing camptothecin and camptothecin analogs in high yield in a totally synthetic process.

Another object of the present invention is to provide a process for synthesizing camptothecin and camptothecin analogs which does not suffer from problems associated with the insolubility of intermediate compounds.

A further object of the invention is to provide a process for the preparation of camptothecin and camptothecin analogs which can be easily modified to produce a variety of analog structures.

Still a further object of the present invention is to provide camptothecin analogs which show good antitumor activity and other desirable biological activities.

These objects and other objects of the present invention which will become apparent from the following specification have been achieved by the present method for the synthesis of camptothecin and camptothecin analogs, which includes the steps of:

cyclizing a compound of the formula shown below, wherein X is an organic group which is converted to a carbonyl group when treated with an acid,

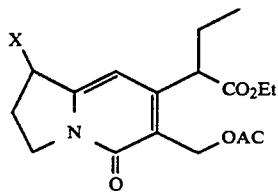

to form a lactone having the formula

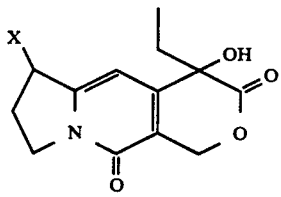

deprotecting said lactone to form a hydroxyl-containing tricyclic compound having the formula shown below, and

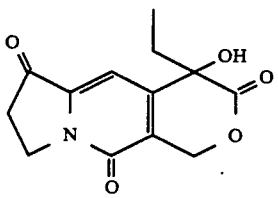

reacting said hydroxyl-containing tricyclic compound with a substituted ortho-amino compound of the formula

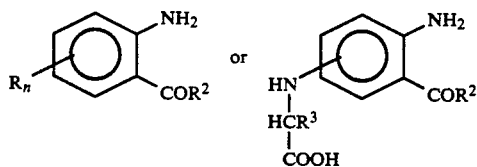

wherein n=1-2 and wherein each R is selected from the group consisting of cyano, methylenedioxy, formyl, hydroxy, $C_{1-8}$ alkoxy, nitro, amino, chloro, bromo, iodo, fluoro, $C_{1-8}$ alkyl, trifluoromethyl, aminomethyl, azido, amido and hydrazino groups; $R^2$ is $H_1$ or $C_{1-8}$ alkyl; and $R^3$ is the side-chain of any of the twenty naturally occurring amino acids.

DETAILED DESCRIPTION OF THE PREFERRED EMBODIMENTS

Figures 1, 1A:
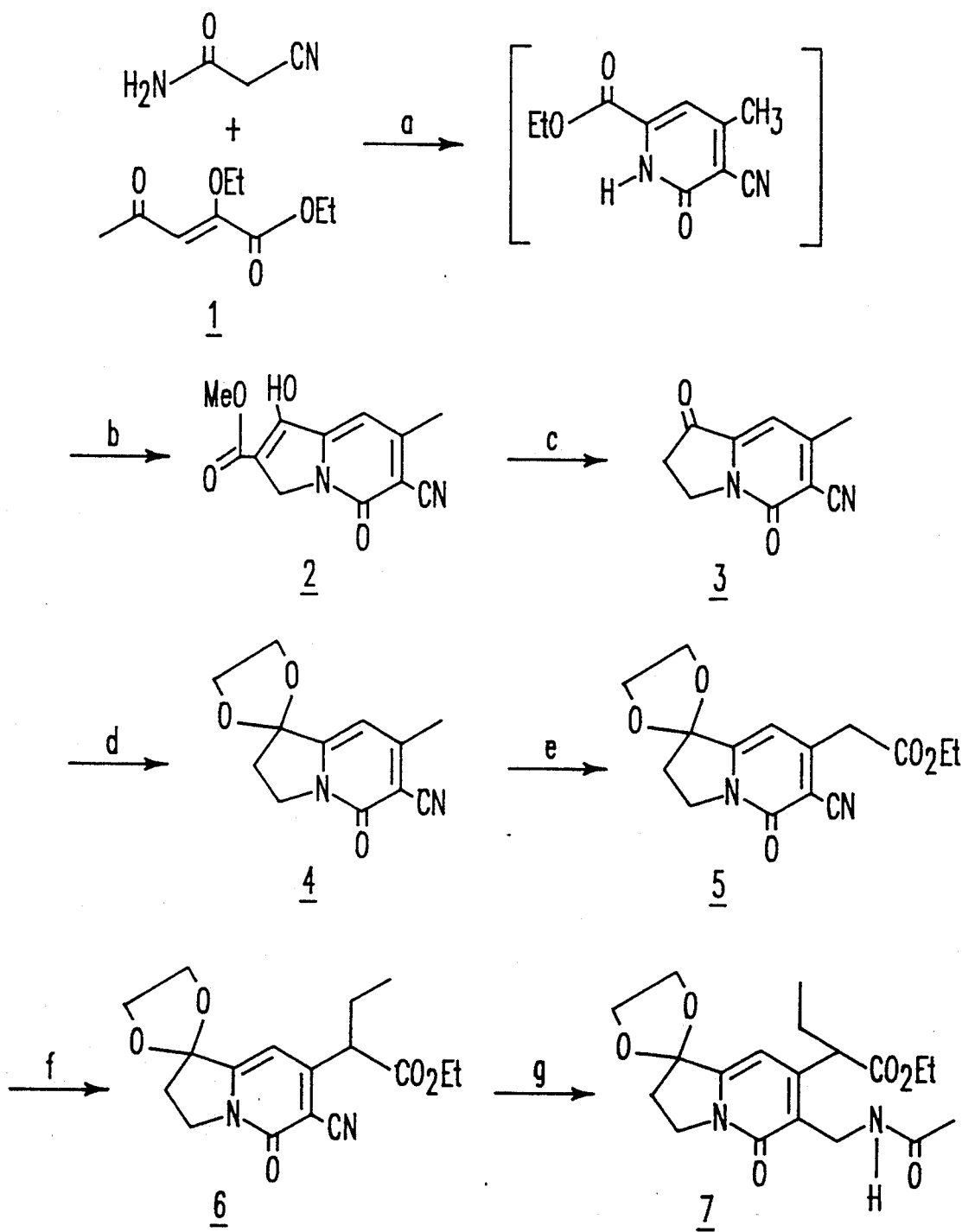
FIGS. 1A-1, 1A-2, and 1B illustrate the synthesis of the hydroxyl-containing tricyclic compound 11, according to the invention.
Figures 1, 1A, 2:
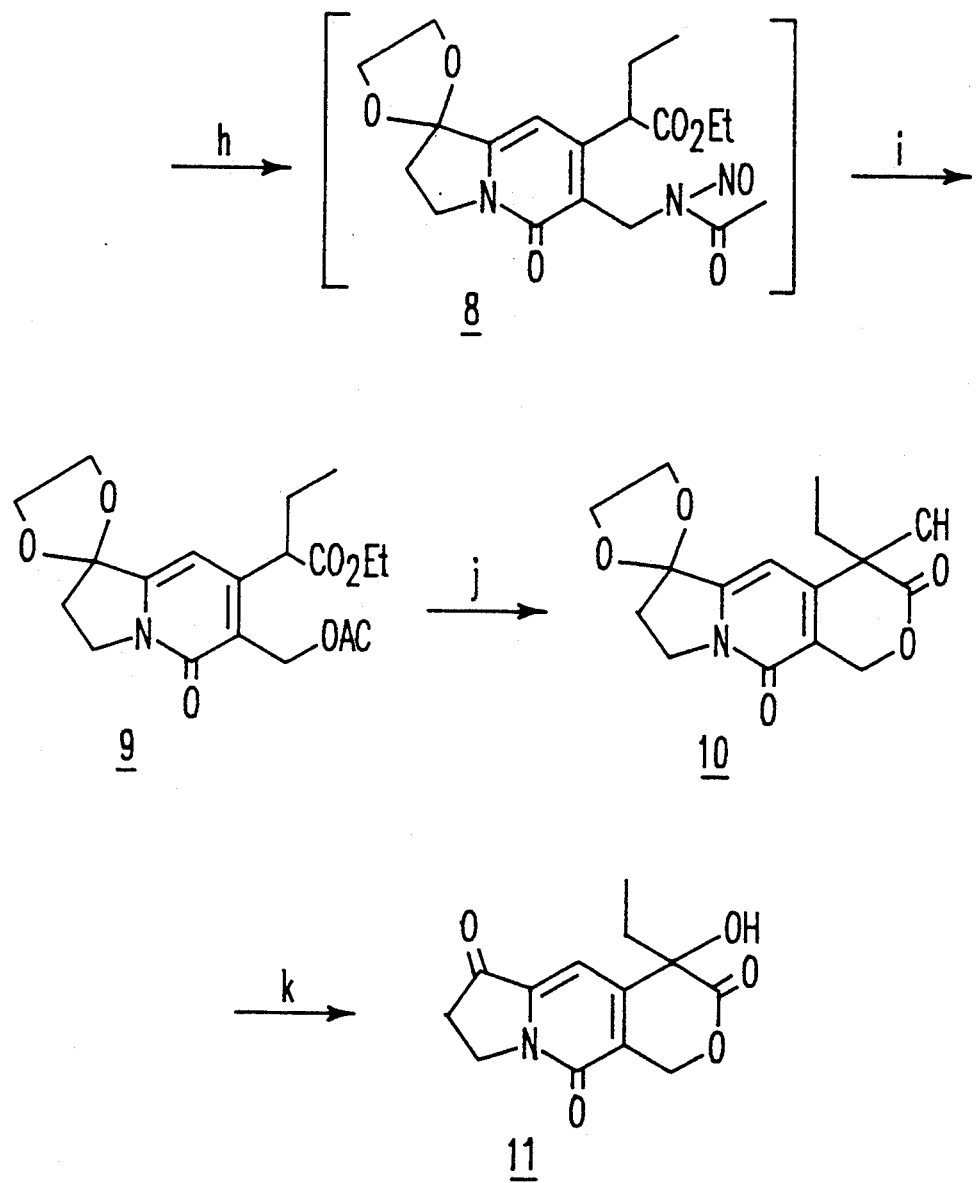
Figure 1B:
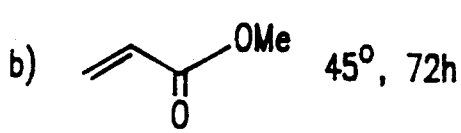

The camptothecin and camptothecin analogs produced by the process of the present invention are racemic, and therefore contain both the (R)-20-hydroxy and (S)-20-hydroxy camptothecin compounds. Naturally occurring camptothecin belongs to the 20(S) series of compounds. Therefore, the compounds produced by the process of the present invention contain a mixture of the natural and non-naturally occurring compounds.

The camptothecin analogs of the present invention have the basic camptothecin structural framework shown below in which the A ring is substituted.

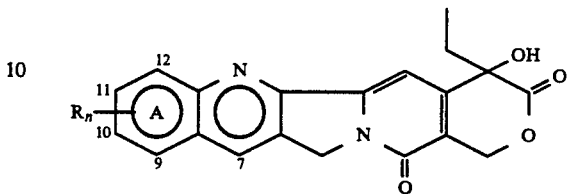

Substituents within the scope of the present invention include hydroxy, nitro, amino, chloro, bromo, iodo, fluoro, $C_{1-8}$ alkyl, $C_{1-8}$ alkoxy, trifluoromethyl, aminomethyl, amido, hydrazino, azido, formyl, and cyano groups as well as groups comprising amino acids and/or peptides bonded to the aromatic ring via the aminonitrogen atom or via an amide linkage which contains the carbonyl group of the amino acid, i.e., an amino acid amido group. Amides prepared from cyclic anhydrides may also be prepared. Preferred alkyl groups include methyl, ethyl, propyl, butyl, isopropyl, isobutyl and sec-butyl groups. Preferred alkoxy groups include methoxy, ethoxy, propoxy and isopropoxy groups.

The preferred amino acid groups are the 20 naturally occurring amino acids having an (L) configuration. These amiono acids are well known to those skilled in the art.

Water-soluble camptothecin analogs which can be prepared by the process of the present invention include analogs in which $R_n$ is an amide linkage formed by reacting an amino-camptothecin analog with the free carboxylic acid group of an amino acid, peptide or carboxylic acid derivative thereof. These amide derivatives may be present as the free amines, i.e., the α-amino group or as any of the well known acid addition salts, such as, for example, hydrochloride, gluconate, phosphate or hydrobromide addition salts. Additional water soluble analogs can be prepared by reacting an amino-camptothecin analog with a cyclic carboxylic acid anhydride to give a carboxylic acid amide group. This reaction results in an amide substituent on the camptothecin structural framework and a free carboxylic acid group which may be present as the free acid or as a salt, e.g., alkali metal or alkaline-earth metal salt, or as an organic cation, e.g., ammonium salts. Preferred anhydrides are the $C_{4-10}$ saturated and unsaturated acid anhydrides. Alternatively, the above water soluble derivatives can also be prepared by employing the corresponding ester-acid halide in place of the anhydride. Water soluble urea and urethane analogs can also be prepared by reacting an amino-camptothecin analog with phosgene followed by an appropriate diamine, e.g. n-alkylpiperazine or an appropriate tertiary-amino alcohol, e.g. n-dialkyl-aminoethannol respectively. These water soluble derivatives are particularly important since they may be therapeutically administered in aqueous pharmaceutical compositions.

Additionally, water soluble dialkylamino ether analogs of camptothecin can be prepared by reacting an appropriate tertiary-aminoalkyl halide, e.g. dialklaminoethyl halide with an hydroxy-camptothecin analog followed by salt formation as described above.

Additionally, two substituents on the A ring may be joined together to form a bifunctional substituent such as the methylenedioxy group. Methylenedioxy substituents may be bonded to any two consecutive positions in the A ring, for example, the 9,10; 10,11 or 11,12 positions.

Preferred substituents include the hydroxy, amino, cyano, methylenedioxy, 9 or 10-glycinamido, 9-or 10-succinamido, 9-or 10-(4-methylpiperazino) carbonylamino, 9-or 10-(N,N-diethylaminoethoxy) carbonylamino, and 9-diethylaminoethoxy substituents. A particularly preferred substituent is the methylenedioxy group.

Particularly preferred compounds within the scope of the invention include 11-methoxy-20(RS)-camptothecin, 11-hydroxy-20(RS)-camptothecin, 10-hydroxy-20(RS)-camptothecin, 9-methoxy-20(RS)-camptothecin, 9-hydroxy-20(RS)-camptothecin, 10-nitro-20(RS)-camptothecin, 10-amino-20(RS)-camptothecin, 9-nitro-20(RS)-camptothecin, 9-amino-20(RS)-camptothecin, 11-nitro-20(RS)-camptothecin, 11-amino-20(RS)-camptothecin, 10,11-dihydroxy-20(RS)-camptothecin, 10-chloro-20(RS)-camptothecin, 10-methyl-20(RS)-camptothecin, 11-formyl-20(RS)-camptothecin and 11-cyano-20(RS)-camptothecin, 10,11-methylenedioxy-20(RS)-camptothecin, 9-or 10-glycinamido-20(RS)-camptothecin, 9-or 10-succinamido-20(RS)-camptothecin, 9- or 10-(4-methylpiperazino) carbonylamino-20(RS)-camptothecin, 9-or 10-(N,N-diethylaminoethoxy) carbonylamino-20(RS)-camptothecin, and 9-diethylaminoethoxy-20(RS)-camptothecin.

Also included within the scope of the present invention are compounds in which the A ring of the camptothecin structure is modified to contain a hetero atom. The modified structures can have an A ring which contains 5 or 6 atoms and the hetero atom may be a nitrogen, sulfur or oxygen atom. These compounds may be represented by the general structure shown below in which the A ring is an aromatic 5 or 6 membered ring containing the hetero atom X.

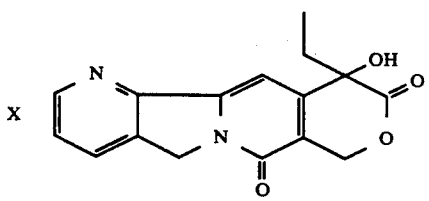

Preferred compounds having a modified A ring structure include compounds in which the A ring is a 6 membered nitrogen-containing aromatic ring and compounds in which the A ring is a 5 membered sulfur-containing aromatic ring. Particularly preferred compounds are 10-aza-20(RS)-camptothecin and A-nor-9-thia-20(RS)-camptothecin.

The camptothecin analogs noted above may be synthesized according to the method of the present invention by reacting a tricyclic compound containing a 20-hydroxyl group with an appropriately substituted ortho-amino aromatic aldehyde or ketone. Camptothecin analogs having an alkyl substituent on $C_7$ are produced when the appropriate ortho-amino ketone is used.

An important step in the method of the present invention is the synthesis of the hydroxyl-containing tricyclic compound having the formula I shown below and in which R is a hydroxyl group.

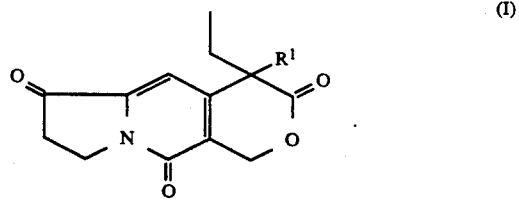

A synthetic method previously developed by the present inventors (J. Med. Chem., 23, 554 (1980)) utilized a related by structurally different tricyclic compound (formula I, R=H). In that method, the tricyclic compound was reacted with a suitable orthoaminoaldehyde under alkaline or acidic conditions to yield a desoxycamptothecin. The desoxycamptothecin was then reacted with oxygen to give camptothecin analogs in which R is OH. A major disadvantage of this procedure is the insolubility of the desoxycamptothecin and its analogs, requiring large solvent volumes in the final step and giving poor yields of the oxygenation product.

In contrast, the method of the present invention synthesizes the key tricyclic intermediate (11) according to FIG. 1. The synthesis of compounds 1-9 was disclosed in Wani et al, J. Med. Chem., 23, 554 (1980). In further contrast to the previous synthesis, the present method introduces the 20-hydroxyl group earlier in the synthetic sequence and then forms the lactone ring to give compound 10. After deprotection of the carbonyl group, the key hydroxyl-containing tricyclic compound 11 is obtained.

The protection of the carbonyl group in compound 3 can be performed using any appropriate organic protecting group which can be removed or converted into a carbonyl group upon treatment with acid. The carbonyl group is thereby "deprotected". These protecting groups are well known to those familiar with synthetic chemistry, and include acetals, ketals, thioacetals, thioketals, etc. Preferred protecting groups have 2-6 carbon atoms. An especially preferred protecting group is $-OCH_2CH_2O-$.

As a consequence of prior introduction of the hydroxyl group into the tricyclic compound 11, the desired pentacyclic analogs are produced in one step by reaction with the appropriate ortho-amino carbonyl compounds. Both compound 11 and the corresponding ketonic synthons are very soluble in organic solvents whereas the pentacyclic product is insoluble. Hence, the oxygenation step, i.e., the introduction of the hydroxyl group, is conveniently carried out at the tricyclic stage rather than on the insoluble pentacyclic desoxy analogs.

Tricyclic compound 11 is then reacted with a suitably substituted ortho-amino aldehyde or ketone to give a camptothecin analog. Substituted ortho-amino aldehydes and ketones within the scope of the present invention include ortho-amino aldehydes and ketones having at least one additional substituent on the aromatic ring. This substituent may be at one or more of the positions equivalent to the 9, 10, 11 or 12 positions of the A ring of the final camptothecin structure as shown below.

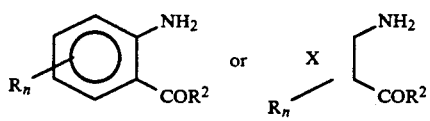

Preferred substituted ortho-amino aldehydes and ketones have substituents in one or more of the equivalent 9, 10, or 11 positions.

The substituents on the substituted ortho-aminoaldehyde or ketone include hydroxy, nitro, amino, $C_{1-8}$ alkyl, chloro, bromo, iodo, fluoro, methylenedioxy ($-O-CH_2-O-$), $C_{1-8}$ alkoxy, trifluoromethyl, aminomethyl, amido, hydrazino, azido, formyl, and cyano groups as well as groups comprising amino acids bonded to the aromatic ring through the amino-nitrogen atom. Preferred examples include the hydroxy, amino, cyano and methylenedioxy substituents. A particularly preferred substituent is the methylenedioxy group.

When an ortho-amino ketone is reacted with tricyclic compound 11, a camptothecin analog having an alkyl substituent at $C_7$ is produced. Preferred ortho-amino ketones are those in which $R^2$ is an alkyl group having 1-8 carbon atoms. Especially preferred ortho-amino ketones are ortho-aminoacetophenone and ortho-aminopropiophenone.

The ortho-amino aldehydes and ketones may be substituted by a group having the formula

$-NH-CHR^3-COOH$ wherein $R^3$ is a side-chain of one of the twenty naturally occurring amino acids. The amino acid substituent is bonded to the aromatic ring via the nitrogen atom and may be bonded to any position on the aromatic ring equivalent to the 9, 10, 11 or 12 positions of the A ring of the final camptothecin structure.

The ortho-amino aldehydes and ketones may be in the free carbonyl form or in a form in which the carbonyl of the aldehyde or ketone is protected by a standard protecting group. These protecting groups are well known to those skilled in the art. Ortho-amino aldehydes and ketones in the free carbonyl form and in the protected carbonyl form are considered within the scope of the present invention and are suitable for use in the present method.

The reaction in which the hydroxyl group is introduced into the tricyclic intermediate compound, i.e., the cyclizing step, can be effected by any suitable reaction which will introduce the hydroxyl group at the appropriate position of compound 9 without causing significant side reactions such as degradation of compound 9 itself.

The reaction is preferably conducted in the presence of a basic catalyst. Suitable basic catalysts include both inorganic and organic bases. Preferred inorganic bases include, for example, sodium and potassium carbonate and sodium and potassium bicarbonate. Preferred organic bases include hindered bases such as triethylamine and diisopropylamine. A particularly preferred basic catalyst is potassium carbonate.

The reaction in which the hydroxyl group is introduced can be performed in the presence of any polar or non-polar solvent in which the reactants are suitably soluble to react. Preferred are polar organic solvents such as methanol, ethanol, propanol, butanol and dimethylformamide. Ether solvents, including crown ethers may also be used.

The oxygen of the hydroxyl group is generally derived from molecular oxygen which is bubbled through the reaction solution. Although the use of oxygen is preferred, other sources of oxygen, such as air, may also be used. Other oxidizing agents such as hydrogen peroxide, lead tetraacetate and selenium dioxide may also be employed.

This reaction is preferably conducted at room temperature although the specific reaction temperature will be dependent on the specific reaction conditions and reactants used.

The deprotection of the carbonyl group in compound 10 is accomplished by treatment with acid. Suitable acids include mineral acids such as HCl, $H_2SO_4$, $HNO_3$, and $H_3PO_4$, as well as organic acids such as alkanoic acids having 1-10 carbon atoms, preferably acetic acid, and $C_{1-12}$ arylsulfonic acids, especially p-toluenesulfonic acid. The deprotection of a carbonyl group in this manner is well known to those skilled in the art.

The tricyclic compound 11 is then reacted with a substituted ortho-amino aldehyde or ketone in the presence of an acid or base catalyst. The base catalyst is preferably any of the base catalysts noted above in cyclizing compound 9 to form compound 10, i.e., for the introduction of the hydroxyl group into tricyclic compound 11. The acid catalyst is preferably a mineral acid such as for example HCl, $H_2SO_4$, $HNO_3$, and $H_3PO_4$, or organic acids such as $C_{1-8}$ alkanoic acids and $C_{1-12}$ arylsulfonic acids, especially p-toluenesulfonic acid.

The reaction of compound 11 with an appropriate ortho-amino compound may be carried out near or in the presence of a polar or non-polar solvent. Preferred polar solvents are the $C_{1-6}$ alcohols, ethers and dimethylformamide. Preferred non-polar solvents are branched or straight chained alkyl hydrocarbons having 4-10 carbon atoms and aromatic hydrocarbons having 6-20 carbon atoms. An especially preferred solvent is toluene.

The reaction of the hydroxyl-containing tricyclic compound with the optionally substituted ortho-amino compound is generally conducted with heating at reflux. Reaction times will vary depending on the particular reactants but are generally in the range from about 10 minutes to 24 hours. Preferred reaction times are in the range of 2-10 hours.

The camptothecin analogs of the present invention have excellent biological activity. As used herein, "biological activity" refers to the ability of the camptothecin analogs to inhibit topoisomerase enzymes, in particular topoisomerase I, and their ability to exert anti-leukemic activity. Anti-leukemic activity may be determined by the ability of the respective compounds to inhibit L-1210 mouse leukemia cells. Although anti-leukemic activity is demonstrated here by the activity of the particular compounds against L-1210 mouse leukemia cells, other known anti-leukemic and anti-tumor in vitro and in vivo models may be used as well to determine anti-leukemic activity.

The mouse anti-leukemic activity of the various ring A oxygenated camptothecin analog is shown in Table I. Similar data for nitrogen analogs and for ring A modified analogs are shown in Tables II and III, respectively. In most cases camptothecin or an analog with well-defined activity was also assayed at the same time as a positive control, and the data are shown in the table footnotes. In this manner the relative antileukemic activity of the various compounds can be compared. The biological activity of additional camptothecin analogs is described in *J. Med. Chem.*, 23, pages 554–560 (1980) incorporated herein by reference.

The ability of camptothecin to inhibit topoisomerase I has been shown. See *J. Biol. Chem.*, 260, 14873–73 (1985) incorporated herein by reference.

may contain any quantity of a camptothecin analog which is effective to inhibit topoisomerase I in vitro or in vivo or exhibit anti-leukemic activity in vivo. Mammals such as humans are treatable with the inventive compositions. Typical in vivo doses within the scope of the invention are from 0.1–60 mg of camptothecin analog per kg of body weight. A particularly preferred

TABLE I

Comparative Activities and Potencies of Ring A Oxygenated Camptothecin Analogues in Mouse Leukemia Assays[a,b]

| Camptothecin derivative | max % T/C (dose, mg/kg) | no. cures out of 6 | $K_E$[c] at max % T/C | active dose range, mg/kg | toxic dose, mg/kg |
|---|---|---|---|---|---|
| 10-OH-20(S)[a,d] | 297 (3.1) | 0 | | 0.4[e]–3.1 | 6.25 |
| 10-OMe-20(S)[a,d] | 167 (1.6) | 0 | | 0.4[e]–1.6 | 3.1 |
| 11-OH-20(RS)[b,f] | 357 (60.0) | 3 | ≥5.68 | 7.5[e]–60.0[g] | >60.0 |
| 10,11-diOMe-20(RS)[b,h] | inactive | | | | >50.0[g] |
| 10,11-OCH$_2$O-20(RS)[b,i] | 325 (2.0) | 2 | ≥5.97 | 2.0[e]–4.0 | >8.0 |
| 10-OCH$_2$CO$_2$Na-20(S)[a,d] | inactive | | | | |
| 10-Et$_2$N(CH$_2$)$_2$O-20(S)[a,d] | 183 (16.0) | 0 | | 2.0[e]–32.0[g] | >32.0 |

[a]Denotes testing in P-388 system; treatment schedule Q04DX03; % T/C = survival time of treated/control animals × 100; IP using Klucel emulsifier.
[b]Denotes testing in L-1210 system; treatment schedule Q04DX02; % T/C = survival time of treated/control animals × 100; IP using Klucel emulsifier.
[c]Log$_{10}$ of initial tumor cell population minus log$_{10}$ of tumor cell population at end of treatment.
[d]20(S)-Camptothecin and 20(S)-camptothecin sodium were used as reference standards; for 20(S)-camptothecin, % T/C (4.0 mg/kg) = 197; for 40(S)-camptothecin sodium, % T/C (40.0 mg/kg) = 212.
[e]Lowest dose administered.
[f]20(S)-camptothecin and 20(S)-camptothecin sodium were used as reference standards: for 20(S)-camptothecin, % T/C (8.0 mg/kg) = 164; for 20(S)-camptothecin sodium, % T/C (40.0 mg/kg) = 178.
[g]Highest dose administered.
[h]20(S)-camptothecin sodium was used as a reference standard: % T/C (25.0 mg/kg) = 206.
[i]20(S)-camptothecin was used as a reference standard: % T/C (5 mg/kg) = 166.

TABLE II

Comparison of Activities and Potencies of Ring A Nitrogen Substituted and Ring A Nitrogen/Oxygen Disubstituted Analogues in L-1210 Mouse Leukemia Assays[a]

| Camptothecin derivative | max % T/C (dose, mg/kg) | no. cures out of 6 | $K_E$[b] at max % T/C | active dose range, mg/kg | toxic dose, mg/kg |
|---|---|---|---|---|---|
| 10-NO$_2$-20(RS)[c] | 219 (15.5) | 1 | ≥5.86 | 7.5[d]–15.5 | 31.0 |
| 10-NH$_2$-20(RS)[c] | 329 (8.0) | 3 | ≥5.86 | 4.0[d]–16.0 | 32.0 |
| 10-NHAc-20(RS)[c] | 318 (40.0) | 1 | ≥5.86 | 5.0[d]–40.0[e] | >40.0 |
| 9-NO$_2$-20(S)[f] | 348 (10.0) | 5 | ≥5.86 | 2.5[d]–20.0 | 40.0[e] |
| 12-NO$_2$-20(S)[f] | 151 (40.0) | 0 | 0.34 | 2.5[d]–40.0[e] | >40.0 |
| 9-NH$_2$-20(S)[f] | 348 (2.5) | 4 | ≥5.86 | 2.5[d]–5.0 | 10.0 |
| 12-NH$_2$-20(S)[f] | inactive | | | | |
| 9-NO$_2$-10-OMe-20(S)[f] | 160 (40.0) | 0 | 1.03 | 2.5[d]–40.0[e] | >40.0 |
| 9-NH$_2$-10-OMe-20(S)[f] | 186 (40.0) | 0 | 2.92 | 2.5[d]–40.0[e] | >40.0 |
| 9-NO$_2$-10-OH-20(S)[f] | 131 (20.0) | 0 | −1.12 | 2.5[d]–40.0[e] | >40.0 |
| 9-NHAc-10-OH-20(S)[f] | 220 (40.0) | 0 | 5.50 | 2.5[d]–40.0[e] | >40.0 |

[a]Treatment schedule Q04DX2; % T/C = survival time of treated/control animals × 100; IP using Klucel emulsifier.
[b]Log$_{10}$ of initial tumor cell population minus log$_{10}$ of tumor cell population at end of treatment.
[c]20(S)-Camptothecin (1) and 10-hydroxy-20(S)-camptothecin (2) were used as reference standards: for 1, % T/C (8.0 mg/kg) = 197; for 2, % T/C (24.0 mg/kg) = 230.
[d]Lowest dose administered.
[e]Highest dose administered.
[f]Compounds 1 and 2 were used as reference standards: for 1, % T/C (10.0 mg/kg) = 267; for 2, % T/C (20.0 mg/kg) = 348.

TABLE III

Comparative Activities of Ring A Modified and Homologated Camptothecin Analogues in Mouse Leukemia Assays[a,b]

| Camptothecin derivative | max % T/C (dose, mg/kg) | no. cures out of 6 | $K_E$[c] at max % T/C | active dose range, mg/kg | toxic dose, mg/kg |
|---|---|---|---|---|---|
| 10-aza-20(RS)[a,d] | 162 (2.5) | 0 | 1.61 | 1.25[e]–2.5 | 5.0 |
| 12-aza-20(RS)[b,f] | 175 (32.0) | 0 | | 8.0–32.0 | >32.0 |
| A-nor-9-thia-20(RS)[a,d] | 193 (25.0) | 0 | −0.94 | 3.12[e]–25.0 | 50.0[g] |

[a]Denotes testing in L-1210 system; treatment schedule Q04DX2; % T/C survival time of treated/control animals × 100; IP using Klucel emulsifier.
[b]Denotes testing in P-388 system; treatment schedule Q04DX3; % T/C = survival time of treated/control animals × 100; IP using Klucel emulsifier.
[c]Log$_{10}$ of initial tumor cell population minus log$_{10}$ of tumor cell population at end of treatment.
[d]20(S)-Camptothecin sodium was used as a reference standard: % T/C (40.0 mg/kg) = 215.
[e]Lowest dose administered.
[f]20(S)-Camptothecin was used as a reference standard: % T/C (4.0 mg/kg) = 197.
[g]Highest dose administered.

Pharmaceutical compositions containing the novel camptothecin analogs are also within the scope of the present invention. These pharmaceutical compositions range is 1–40 mg/kg.

There may also be included as part of the composition pharmaceutically compatible binding agents, and/or adjuvant materials. The active materials can also be mixed with other active materials which do not impair the desired action and/or supplement the desired action. The active materials according to the present invention can be administered by any route, for example, orally, parenterally, intravenously, intradermally, subcutaneously, or topically, in liquid or solid form.

A preferred mode of administration of the compounds of this invention is oral. Oral compositions will generally include an inert diluent or an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.1% of active compound but may be varied depending upon the particular form.

The tablets, pills, capsules, troches and the like may contain the following ingredients: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotes; a glidant such as colloidal silicon dioxide; and a sweetening agent such as sucrose or saccharin or flavoring agent such as peppermint, methyl salicylate, or orange flavoring may be added. When the dosage unit form is a capsule, it may contain, in addition to material of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active ingredient may be incorporated into a solution or suspension.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic.

The dosage values will vary with the specific severity of the disease condition to be alleviated. Good results are achieved when the compounds described herein are administered to a subject requiring such treatment as an effective oral, parenteral or intravenous dose. It is to be understood that for any particular subject, specific dosage regimens should be adjusted to the individual need and the professional judgment of the person administering or supervising the administration of the aforesaid compound. It is to be further understood that the dosages set forth herein are exemplary only and they do not limit the scope or practice of the invention. The dosages may be administered at once, or may be divided into a number of smaller doses to be administered at varying intervals of time.

Other features of the invention will become apparent in the course of the following descriptions of exemplary embodiments which are given for illustration of the invention and are not intended to be limiting thereof.

EXAMPLES

Synthesis of Tricyclic Compound 11

6-Cyano-7-methyl-1,5-dioxo-$\Delta^{6(8)}$-tetrahydroindolizine (Compound 3)

Ethyl acetopyruvate was prepared from acetone and diethyl oxalate as described in *Org. Synthesis*, Coll. Vol. 1, 238 (1958). Further reaction with triethylorthoformate and ammonium chloride in ethanol afforded the known enol ether 1. See L. Claisen, *Chem. Ber.*, 40, 3903 (1907).

Ethyl(2-ethoxy-4-oxo)-pent-2-enoate(1) (100.01 g, 0.538 mol) was added gradually to a preheated (45°), mechanically stirred mixture of $K_2CO_3$ (79.04 g, 0.573 mol) and cyanoacetamide (48.46 g, 0.577 mol) in DMF (960 mL). The mixture was kept at 45° for 18 h, whereupon the thick, red slurry was treated dropwise with freshly distilled methyl acrylate (360 mL, 343 g, 3.99 mol). After 72 hr at 45°, the red suspension was filtered, dissolved in 5 liters of water, and acidified to pH 1.5 with concentrated HCl. Crude bicyclic ester 2 (127.98 g) was collected by filtration as a pink solid. Without further treatment, 2 was refluxed in a solution concentrated of HCl (800 ml) and glacial HOAc (800 ml) for 2 hr. Removal of the solvents in vacuo gave the bicyclic pyridone 3 (39.66 g, 39% based on 1).

6-Cyano-1,1-(ethylenedioxy)-7-methyl-5-oxo-$\Delta^{6(8)}$-tetrahydroindolizine (Compound 4)

Compound 3 (10.54 g, 0.056 mol) as a stirred solution in $CH_2Cl_2$ (500 ml) was treated at room temperature under $N_2$ with ethylene glycol (6.85 ml, 7.63 g, 0.123 mol) and $Me_3SiCl$ (31.30 ml, 26.39 g, 0.247 mol) and left at ambient temperature (20°) for 65 hr. The solution was filtered to remove some black suspended material before washing with 1M aq NaOH solution. The organic phase was washed with brine, filtered through Celite and evaporated to afford ethylene ketal 4 (10.26 g, 79%) as a pink solid.

6-Cyano-1,1-(ethylenedioxy)-7-[(ethoxycarbonyl)methyl]-5-oxo-$\Delta^{6(8)}$-tetrahydroindolizine (Compound 5)

The ketal 4 (5.0 g, 0.022 mol) was refluxed in a suspension of KH (11.9 g, 0.068 mol) in toluene (40 mL) for 10 min. Diethyl carbonate (6.79 g, 0.058 mol) and a catalytic amount (0.31 g, 6.7 mmol) of absolute ethanol were added and refluxing continued for 3 hr. The dark solid was crushed and the resulting suspended salt of 5 was collected by filtration. The salt was neutralized by the careful addition of cold aqueous HOAc. Water was added and the product extracted into $CH_2Cl_2$. Following a wash with brine and drying ($Na_2SO_4$), evaporation of the $CH_2Cl_2$ afforded crude 5. Purification by silica gel chromatography (2% MeOH in $CHCl_3$) and recrystallization (MeOH) gave pure 5 (4.97 g, 76%).

6-Cyano-1,1-(ethylenedioxy)-7-[1'(ethoxycarbonyl)-propyl]-5-oxo-$\Delta^{6(8)}$-tetrahydroindolizine (Compound 6)

A stirred solution of the ester 5 (4.01 g, 0.0132 mol) in anhydrous DME (70 mL) at −78° C. was treated with potassium tert-butoxide (1.7 g, 15 mmol). After 5 min, EtI (8.24 g, 0.053 mol) was added over a 5 min period. After stirring for 1.5 hr at −78° C., the mixture was left to warm to room temperature overnight. Water was added and the product extracted into $CH_2Cl_2$. After washing with brine and drying ($Na_2SO_4$), $CH_2Cl_2$ was evaporated to give the ester 6 (4.3 g, 98%).

6-(Acetamidomethyl)-1,1-(ethylenedioxy)-7-[1′-(ethoxycarbonyl)propyl]-5-oxo-$\Delta^{6(8)}$-tetrahydroindolizine (Compound 7)

A solution of the ester ketal 6 (2.0 g, 6.0 mmol) in acetic anhydride (30 mL) and HOAc (10 mL) was hydrogenated for 6 hr at 45° C. under 50 psi in the presence of Raney nickel (3 g; washed with HOAc). The catalyst was removed by filtration and the solvent removed in vacuo to give 7 (2.3 g, 100%) as an oil. Purification by silica gel column chromatography (2% MeOH in $CHCl_3$) gave pure 7 as an oil.

6-(Acetoxymethyl)-1,1-(ethylenedioxy)-7-[1′-(ethoxycarbonyl)propyl]-5-oxo-$\Delta^{6(8)}$-tetrahydroindolizine (Compound 9)

A cooled solution of amide 7 (2.3 g, 6.0 mmol) in $Ac_2O$ (30 mL) and HOAc (10 mL) was treated with $NaNO_2$ (1.8 g, 26 mmol) and the reaction mixture stirred for 2 h at 0° C. Inorganic salts were removed by filtration and the solvent removed in vacuo at room temperature to afford the N-nitroso intermediate 8 as an oil. Compound 8 was converted directly to the title acetoxy compound 9 by refluxing overnight in $CCl_4$. The solution was washed with water, dried ($Na_2SO_4$) and the solvent removed in vacuo to give 9 (2.3 g 100%) as an oil.

1,1′Ethylenedioxy-5-oxo-(5′-ethyl-5′-hydroxy-2′H,5′H,6′H-6-oxopyrano)-[3′,4′-f]-$\Delta^{6,8}$-tetrahydroindolizine (Compound 10)

Oxygen was bubbled through a mixture of 6-(acetoxymethyl)-1,1-(ethylenedioxy)-7-[1′-ethoxycarbonyl)-propyl]-5-oxo-$\Delta^{6,8}$-tetrahydroindolizine (Compound 9, 405 mg, 1.07 mmol), anhydrous $K_2CO_3$ (148 mg 1.07 mmol) and methanol (7.5 mL) for 24 hr. The solution was cooled in an ice bath and made acidic (pH 2-4) by addition of 1N $H_2SO_4$. Most of the methanol was removed in vacuo at room temperature, and water (20 mL) was added. The aqueous solution was extracted with $CH_2Cl_2$ (3×20 mL), dried ($NaSO_4$) and evaporated to give a solid which was crystallized from $CH_2Cl_2$-hexane to give 280 mg (85%) of 10: mp 179°-181° C.; $\nu_{max}$ ($CHCl_2$) 1740, 1660 $cm^{-1}$; $^1$H-NMR ($CDCl_3$) $\delta$0.91 (t, 3, J=7 Hz, $CH_2CH_3$), 1.75 (q, 2, J=7 Hz, $CH_2CH_3$), 2.35 (t, 2, J=6.5 Hz, $CH_2\alpha$ to ketal), 4.1 (m, 6, $OCH_2CH_2O$ and $CH_2N$), 5.30 (m, 2, $ArCH_2O$), 6.87 (s, 1, pyridone). Anal. Calcd for $C_{15}H_{17}NO_6$: C, 58.63; H, 5.54; N, 4.56. Found: C, 58.72, H, 5.68; N, 4.57.

5′RS-1,5-Dioxo-(5′-ethyl-5′-hydroxy-2′H,5′H,6′H-6-oxopyrano)-[3′,4′,f]-$\Delta^{6,8}$-tetrahydroindolizine (Compound 11)

A solution of 10 (3.88 g, 12.6 mmol) in 2N $H_2SO_4$ (50 mL) and DME (50 mL) was heated for 24 hr under $N_2$. The reaction mixture was concentrated to one half its volume in vacuo, diluted with $H_2O$ (100 mL) and extracted with $CH_2Cl_2$ (5×50 mL). The organic layer was dried ($Na_2SO_4$) and evaporated to yield a solid which was crystallized from $CH_2Cl_2$-hexane to yield 2.68 g (80%) of 11 as a light brown solid: mp 185°-187° C.; $\nu_{max}$ ($CHCl_3$) 1750 (shoulder, ketone), 1745 (lactone), 1660 $cm^{-1}$ (pyridone); $^1$H-NMR ($CDCl_3$) $\delta$0.91 (t, 3, J=7 Hz, $CH_2CH_3$), 1.80 (q, 2, J=7 Hz, $CH_2CH_3$), 2.93 (t, 2, J=6.5 Hz, $CH_2C=O$), 4.30 (t, 2, J=6.5 Hz, $CH_2N$), 5.35 (m, 2, $ArCH_2O$), 7.17 (s, 1, aromatic H). Anal. Calcd for $C_{13}H_{13}NO_5$: C, 59.32; H, 4.94; N, 5.32. Found: C, 59.12, H, 4.91; N, 5.16.

Synthesis of Camptothecin Analogs

Synthesis of 11-hydroxy-20(RS)-camptothecin 11-hydroxy-20(RS)-camptothecin is prepared from 11-methoxy-20(RS)-camptothecin by demethylation of the latter with hydrobromic acid as follows:

11-Methoxy-20(RS)-camptothecin

A mixture of 4-methoxy-2-aminobenzaldehyde (180 mg, 1.19 mmol) and the tricyclic ketone 11 (300 mg, 1.14 mmol) in toluene (18 mL) was heated under $N_2$ in a flask equipped with a Dean-Stark trap. At reflux p-toluenesulfonic acid (5 mg) was added, and the red-brown solution was heated for an additional 2 hr. The toluene was removed under reduced pressure to give a brown solid which was treated with water (10 mL) and chloroform (20 mL). The aqueous phase was extracted with additional chloroform (3×20 mL) and the combined extracts dried ($Na_2SO_4$). Evaporation gave a brown solid which was recrystallized from methanol-chloroform to give 216 mg (50%) of compound as a tan solid: 275°-279° C.; mass spectrum (electron impact), m/z 378.1219$M^+$; $C_{21}H_{18}N_2O_5$ requires 378.1214; $\nu_{max}$ (KBr) 3480 (OH), 1745 (lactone), 1660 (pyridone), 1622, 1236 and 1152 $cm^{-1}$; $^1$H-NMR (DMSO-$d_6$) $\delta$0.87 (t, 3, J=7 Hz, H-18), 1.85 (m, 2, H-19), 3.95 (s, 3, 11-$OCH_3$), 5.24 (s, 2, H-5), 5.42 (s, 2, H-17), 7.32 (s, 1, H-14), 7.37 (dd, 1, J=9, 2.5 Hz, H-10), 7.56 (d, 1, J=2.5 Hz, H-12), 8.02 (d, 1, J=9 Hz, H-9), 8.60 (s, 1, H-7).

11-Hydroxy-20(RS)-camptothecin 11-methoxy-20(RS)-camptothecin (75 mg) was combined with 48% aqueous HBr (2.5 mL) and heated at reflux for 6 hr. The red-brown mixture was stripped of solvent under high vacuum. Chromatography of the residue through silica gel (15 g) (7% MeOH-$CHCl_3$) gave the 11-hydroxy compound (33 mg, 45%) which was further purified by recrystallization from 13% MeOH in $CHCl_3$: mp 323°-326° C.; mass spectrum (electron impact), m/z 364.1054 $M^+$, $C_{20}H_{16}N_2O_5$ requires 364.1059; $\nu_{max}$ (KBr) 3450, 1742, 1654, 1613, 1592, 1570, 1245 $cm^{-1}$; $\nu_{max}$ (EtOH), 224 (log $\epsilon$ 4.58), 259, (4.39), 353 (4.16), 371 (4.19), 387 (4.20); $^1$H-NMR (DMSO-$d_5$): $\delta$0.88 (t, 3, J=7 Hz, H-18), 1.85 (m, 2, H-19), 5.20 (s, 2, H-5), 5.41 (s, 2, H-17), 6.51 (br s, 1, OH-20), 7.26 (dd, 1, J=9, 2.5 Hz, H-10), 7.28 (s, 1, H-14).

10-Hydroxy-20(RS)-camptothecin

This compound is prepared in a manner analogous to that described for the 11-hydroxycamptothecin using 5-methoxy-2-aminobenzaldehyde which is reacted with the tricyclic ketone 11 in the presence of p-toluenesulfonic acid. The product is 10-methoxy-20(RS)-camptothecin which on treatment with refluxing hydrobromic acid as described for 11-hydroxy-camptothecin, gives 10-hydroxy-20(RS)-camptothecin.

9-Methoxy-20(RS)-camptothecin and 9-Hydroxy-20(RS)-camptothecin

In a manner analogous to that described for 11-methoxy-20(RS)-camptothecin, 6-methoxy-2-aminobenzaldehyde is treated with the tricyclic 11 ketone in the presence of p-toluenesulfonic acid yielding 9-methoxy-20(RS)-camptothecin. Demethylation with hydrobromic acid gives 9-hydroxy-20(RS)-camptothecin.

10-Nitro-20(RS)-camptothecin

A mixture of 2-amino-5-nitrobenzaldehyde (95 mg, 0.57 mmol) and the tricyclic ketone 11 (150 mg, 0.57 mmol) was heated at 120° C. for 10 min. The temperature was raised to 160° C., and the dark molten mass was kept at this temperature for 1.5 hr with occasional stirring. Chromatography of the residue through silica gel (20 g) using 0.5% MeOH in CHCl$_3$ afforded the title compound (108 mg) as a yellow solid; mp 297°-300° C. (decomp.); mass spectrum (electron impact), m/z 393.0965 M+, C$_{20}$H$_{15}$N$_3$O$_6$ requires 393.0960; $\nu_{max}$ (KBr) 3450 (OH), 1745 (lactone), 1660 (pyridone), 1620, 1350, and 1160 cm$^{-1}$; $^1$H-NMR (TFA-d$_1$) δ1.14 (t, 3, J=7 Hz, H-18), 2.15 (m, 2, H-19), 5.88 (s, 2, H-5), 5.68 (Abq, 2, J=17 Hz, Δγ=85 Hz, H-17), 8.43 (s, 1, H-14), 8.70 (d, 2, J=8 Hz, H-12), 9.05 (d, 2, J=8 Hz, H-11), 9.35 (s, 1, H-9), 9.60 (s, 1, H-7).

10-Amino-20(RS)-camptothecin

A suspension of 10-nitro-20(RS)-camptothecin (100 mg) and 10% Pd/C (40 mg) in absolute EtOH (40 mL) was stirred in an atmosphere of H$_2$ at room temperature for 30 min. Filtration through Celite and removal of the solvent under reduced pressure gave a tan yellow solid (86 mg crude). Recrystallization from 13% MeOH/CHCl$_3$ gave the pure product (30 mg) as an olive-yellow solid: mp, softening at 135° C., gradual blackening upon further heating; mass spectrum (electron impact), m/z 363.116 M+; C$_{20}$H$_{17}$N$_3$O$_4$ requires 363.1218; $\nu_{max}$ (KBr) 3440 (OH, NH$_2$), 1750 (lactone), 1660 (pyridone) cm$^{-1}$; $^1$H-NMR (TFA-d) δ1.06 (t, 3, J=7 Hz, H-18), 2.08 (d, J=7 Hz, H-17), 5.89 (s, 2, H-5), 5.70 (Abq, 2, J=17 Hz, Δγ=85 Hz, H-17), 8.34 (d, J=9 Hz, H-12), 8.64 (d, J=9 Hz, H-11), 9.26 (s, 1, H-(9), 9.43 (s, 1, H-7).

9-Nitro-20(RS)-camptothecin and 9-Amino-20(RS)-camptothecin

A mixture of 2-amino-6-nitrobenzaldehyde is treated with the tricyclic ketone 11 in the manner described for the 10-nitro series above yielding 9-nitro-20(RS)-camptothecin. This compound, after reduction with palladium/carbon, yielded 9-amino-20(RS)-camptothecin. Alternatively, the 9-amino compound is obtained in one step by reaction of 2,6-diaminobenzaldehyde with ketone 11.

11-Nitro-20(RS)-camptothecin and 11-Amino-20(RS)-camptothecin

In a manner similar to that described for 10-nitro-20(RS)-camptothecin, a mixture of 2-amino-4-nitrobenzaldehyde is treated with the tricyclic ketone 11 yielding 11-nitro-20(RS)-camptothecin which in turn is reduced to 11-amino-20(RS)-camptothecin by palladium/carbon. Alternatively, the 11-amino-20(RS)-camptothecin is obtained by reaction of 2,4-diaminobenzaldehyde with ketone 11.

10,11-Dihydroxy-20(RS)-camptothecin

A solution of the crude dibenzyloxy aminoacetal (400 mg) and the tricyclic ketone 11 (132 mg, 0.5 mmol) in toluene (60 mL) was refluxed for 8 hr. It was filtered hot, and the pure dibenzylether was collected upon cooling (200 mg, 81%); mp 276° C. $\nu_{max}$ (KBr) 3440, 1740, 1650, 1590, 1490, 1440, 1380, 1250, 1140, 1100 cm$^{-1}$; 250 MHz $^1$H-NMR (DMSO-d$_6$) δ0.88 (t, 3, J=7 Hz, H-18), 1.86 (m, 2, H-19), 5.22 (s, 2, H-17), 5.34 (s, 2, 10-OCH$_2$—C$_6$H$_5$), 5.39 (s, 2, 11-OCH$_2$—C$_6$H$_5$), 5.41 (s, 2, H-5), 6.5 (s, 1, OH), 7.25 (s, 1, H-14) 7.35-7.65 (m, 12, H-9, 12, —OCH$_2$—C$_6$H$_5$), 8.44 (s, 1, H-7). Anal. calcd for C$_{34}$H$_{28}$N$_2$O$_6$: C, 72.84; H, 5.03; N, 5.00. Found C, 72.91; H, 5.09; N, 4.96.

The dibenzyl ether (130 mg, 0.23 mmol) was mildly refluxed for 2 hr in 24% HBr (50 mL). The acid was removed, and the residue was dissolved in hot methanol (50 mL). Ether (50 mL) was added at room temperature and the yellow powdery dihydroxy camptothecin hydrobromide was collected (122 mg, 77%) mp>300° C. $\nu_{max}$ (KBr) 3400 (b), 1740, 1655, 1585, 1545, 1510, 1395, 1300, 1270, 1200, 1160 cm$^{-1}$; $^1$H NMR (DMSO, d$_6$): δ0.88 (t, 3, J=7 Hz, H-18), 1.85 (m, 2, H-19), 5.20 (s, 2, H-17), 5.42 (s, 2, H-5), 7.31 (s, 2, H-9, H-14), 7.40 (s, 1, H-12), 8.45 (s, 1, H-7). Anal. calcd for C$_{20}$H$_{17}$BrN$_2$O$_6$. 0.5 H$_2$O: C, 51.08; H, 3.86; N, 5.95; Br, 16.99. Found C, 51.09; H, 4.04; N, 5.78; Br, 16.83.

Dihydroxy hydrobromide salt (110 mg, 0.23 mmol) was suspended in water (10 mL). Sodium hydroxide (0.1 N, 7.2 mL) was added and the mixture was agitated. The resulting clear solution was acidified using 5N HCl; and after an hour, the sample was centrifuged, the supernatant liquid was decanted and the process repeated with additional water (20 mL). The residue was dried (78 mg, 74%); mp>300° C. $\nu_{max}$ (KBr): 3490, 3000 (b), 1740, 1645, 1590, 1460, 1385, 1265, 1190, 1150 cm$^{-1}$. $^1$H NMR (DMSO, d$_6$): δ0.38 (t, 3, J=7 Hz, H-18), 1.87 (q, 2, H-19), 5.20 (s, 2, H-17), 5.42 (s, 2, H-5), 7.35 (s, 1, H-14), 7.44 (s, 1, H-9), 7.52 (s, 1, H-12), 8.51 (s, 1, H-7). Anal. calcd for C$_{20}$H$_{16}$N$_2$O$_6$. 0.75 H$_2$O: C, 61.06; H, 4.44; N, 7.12. Found C, 61.12; H, 4.44; N, 7.09.

10-Chloro-20(RS)-camptothecin

This compound was prepared by treating 5-chloro-2-aminobenzaldehyde with the tricyclic ketone 11.

A solution of the 5-chloro-2-aminobenzaldehyde (80 mg, 0.51 mmol) and the tricyclic ketone 11 (100 mg, 0.38 mmol) in toluene (60 mL) was refluxed for 15 min. p-Toluenesulfonic acid (10 mg) was then added, and refluxing was continued for an additional 5 hr. The solvent was removed in vacuo and the residue chromatographed (silica gel 60, 2% MeOH-CHCl$_3$). The product obtained was recrystallized from CHCl$_3$-MeOH-EtOAc; mp 270° C., 60 mg (41%). $\nu_{max}$ (KBr), 3430, 1745, 1655, 1600, 1495, 1230, 1160 cm$^{-1}$. 250 MHz $^1$H-NMR (TFA-d$_1$) δ1.15 (t, 3, J=7 Hz, H-18), 2.16 (m, 2, H-19), 5.73 (ABq, 2, J=17 Hz, Δγ=85 Hz, H-17), 5.84 (s, 2, H-5), 8.29 (d, 1, J=9 Hz, H-11), 8.35 (s, 1, H-14), 8.40 (s, 1, H-9), 8.45 (d, 1, J=9 Hz, H-12), 9.31 (s, 1, H-7). Anal. calcd for C$_{20}$H$_{15}$ClN$_2$O$_4$ 0.5 H$_2$O: C, 61.47; H, 4.12; N, 7.17; Cl, 9.07. Found C, 61.41; H, 4.12; N, 7.12; Cl, 9.11.

10-Methyl-20(RS)-camptothecin

5-Methyl-2-aminobenzaldehyde was treated with the tricyclic ketone 11 to give the title compound.

The tricyclic ketone 11 (130 mg, 0.5 mmol) and the 5-methyl-2-aminobenzaldehyde (560 mg) in toluene (60 mL) were refluxed for 0.5 hr. Acetic acid (1 mL) and p-toluenesulfonic acid (35 mg) were added, an refluxing was continued for an additional 5 hr. The solvent was removed in vacuo, and the residue was triturated with warm ether (30 mL). The product was recrystallized from chloroform-methanol-ether to yield pure compound (102 mg, 57%), mp 278°–280° C. (KBr) 3460, 2980, 1740, 1655, 1590, 1550, 1470, 1450, 1370, 1260, 1240, 1160, 1050 cm$^{-1}$. 250 MHz $^1$H-NMR (DMSO-d$_6$) δ0.89 (t, 3, J=7 Hz, H-18), 1.87 (q, 2, H-19), 2.54 (s, 3, 10-CH$_3$), 5.24 (s, 2, H-17), 5.42 (s, 1, H-5), 7.31 (s, 1, H-14), 7.69 (d, 1, J=8.6 Hz, H-11), 7.86 (s, 1, H-9), 8.05 (d, 1, J=8.6 Hz; H-12), 8.55 (s, 1, H-7). Anal. calcd for C$_{21}$H$_{18}$N$_2$O$_4$. 0.25 H$_2$O: C, 68.75; H, 5.08; N, 7.64. Found C, 68.74; H, 5.08; N, 7.64.

11-Formyl-20(RS)-camptothecin

2-Nitroterephthaldicarboxaldehyde was converted to the ethylene diacetal by conventional methods and reduced using Na$_2$S. A solution of the nitro diacetal (4.1 g, 17.5 mmol), Na$_2$S (14 g) in 80% ethanol (15 mL) was refluxed for 1 hr. Ethanol was removed in vacuo, the reaction mixture was diluted with water (10 Ml) and the aqueous phase was extracted with CH$_2$Cl$_2$ (4·50 mL). The organic phase was washed with water, dried (MgSO$_4$), and evaporated to give the aminodiacetal, which was recrystallized from ethyl acetatehexane (2.8 g, 78%); mp 76° C. $\nu_{max}$ (KBr) 3480, 3395, 3000, 2960, 2900, 1625, 1445, 1395, 1085, 950 cm$^{-1}$. 60 MHz $^1$H NMR (CDCl$_3$-D$_2$O) δ4.0 (m, 8, —OCH$_2$CH$_2$O—), 5.6 (s, 1, —O—CH—O—, C-4), 5.7 (s, 1, —O—CH—O—, C-1), 6.6 (s, 1, H-3), 6.65 (d, 1, J=8 Hz, C-5), 7.2 (d, 1, J=8 Hz, H-6). Anal. calcd for C$_{12}$H$_{15}$NO$_4$: C, 60.66; H, 6.36; N, 5.90. Found C, 60.79; H, 6.41; N, 5.84.

A solution of the tricyclic ketone 11 (265 mg, 1.0 mmol), aminodiacetal (500 mg, 2.1 mmol), 300 mg initially, 100 mg each at intervals of 5 and 10 hr) in toluene (70 mL) was refluxed for 0.5 hr. Acetic acid (2 mL) was added and refluxing continued for 18 hr. The solvent was evaporated in vacuo, and the residue was taken up in 75% methanol (250 mL). Conc. HCl (3 mL) was added and the reaction mixture heated at 50°–60° C. for 24 hr. The mixture was filtered, and the residue was washed with water and recrystallized from CHCl$_3$-MeOH-EtOAc. mp: 276°–279° C. (175 mg, 45%). $\nu_{max}$ (KBr) 3460, 1745, 1690, 1655, 1600, 1200, 1150, 1135 cm$^{-1}$. 250 MHz $^1$H NMR (TFA-d$_1$), δL, 16 (t, 3, J=7 Hz, H-18) 2.16 (q, 2, J=7 Hz, H-19), 5.78 (ABq, 2, J=18 Hz, Δγ=85 Hz, H-17), 5.89 (s, 2, H-5), 8.43 (s, 1, H-14), 8.66 (d, 1, J=8.5 Hz, H-10), 8.60 (d, 1, J=8.5 Hz, H-9), 9.12 (s, 1, H-12), 9.49 (s, 1, H-7), 10.42 (s, 1, CHO). Anal. calcd. for C$_{21}$H$_{16}$N$_2$O$_5$. H$_2$O: C, 64.01; H, 4.56; N, 7.11. Found C, 64.08, H, 4.21; N, 6.84.

11-Cyano-20(RS)-camptothecin

A mixture of 11-formyl-20(RS)-camptothecin (225 mg, 0.6 mmol), hydroxylamine hydrochloride (50 mg, 0.72 mmol), sodium formate (90 mg, 1.3 mmol), and formic acid (6 mL) was refluxed for 1.5 hr. The mixture was evaporated to dryness in vacuo, and the residue was washed with water, dried and chromatographed (silica gel 60, 0.5% MeOH-CHCl$_3$) and recrystallized from CHCl$_3$-EtOAc to yield the 11-cyano compound (65 mg, 29%): mp 288° C. $\nu_{max}$ (KBr) 3400, 2235, 1735, 1655, 1590, 1450, 1400, 1230, 1150, 1110, 1045 cm$^{-1}$. 250 MHz $^1$H NMR (DMSO-d$_6$): δ0.88 (t, 3, J=7 Hz, H-18), 1.88 (m, 2, H-19), 5.32 (s, 2, H-17), 5.44 (s, 2, H-5), 7.37 (s, 1, H-14), 7.98 (d, 1, J=8.5 Hz, H-10), 8.32 (d, 1, J=8.5 Hz, H-9), 8.74 (s, 1, H-12), 8.80·(s, 1, H-7). Anal. calcd for C$_{21}$H$_{15}$N$_3$O$_4$. 1.5 H$_2$O: C, 62.99; H, 4.52; N, 10.49. Found C, 62.99; H, 3.95; N, 10.20.

Alternatively, 11-cyano-20(RS)-camptothecin can be prepared by the reaction of 5-cyano-2-aminobenzaldehyde with the tricyclic ketone 11.

Preparation Of Camptothecin Analogs With Modified A Ring Structure

The reaction of the tricylic ketone 11 with suitable precursors other than substituted ortho-amino-benzaldehydes can be used to give active new camptothecin analogs exemplified by the following non-limiting examples:

10-Aza-20(RS)-camptothecin

A solution of 4-aminonicotinaldehyde (24.2 mg, 0.198 mmol), the tricyclic ketone 11 (53.5 mg, 0.203 mmol) and p-TsOH. H$_2$O (2 mg) in toluene (25 mL) was refluxed for 4 days using Dean-Stark trap. The solvent was removed under reduced pressure, and the residue was chromatographed through silica gel (20 g) using CHCl$_3$-acetone-MeOH (5:1:1). The product was crystallized from 13% MeOH in CHCl$_3$ and EtOAc: mp 289°–292° C.; mass spectrum (electron impact), m/z 349.1061 M$^+$; C$_{19}$H$_{15}$N$_3$O$_4$ requires 349.1066; $\nu_{max}$ (KBr) 3320 (OH), 1730 (lactone), 1650 (pyridone), 1600 (aromatic) cm$^{-1}$; $^1$H NMR (CDCl$_3$) 1.05 (t, 3, J=7.8 Hz, H-18), 1.92 (m, 2, H-19), 5.35 (s, 2, H-5), 5.52 (ABq, 2, J=18 Hz, Δγ=85 Hz, H-17), 7.74 (s, 1, H-14), 8.04 (d, 1, J=5.5 Hz, H-12), 8.53 (s, 1, H-7), 8.84 (d, J=5.5 Hz, H-11), 9.4 (s, 1, H-9).

A-Nor-9-thia-20(RS)-camptothecin

This sulfur containing camptothecin analog is prepared by the reaction of 3-amino-2-formylthiophene with tricyclic ketone 11.

A solution of 3-amino-2-formylthiophene (79 mg, 0.62 mmol) and the tricyclic ketone 11 (96 mg, 0.37 mmol) in toluene (1.5 mL) was brought to reflux and then cooled before adding a crystal of p-toluenesulfonic acid. The mixture was refluxed for 2.5 hr under N$_2$, cooled and the precipitate filtered. The crude material was chromatographed on silica gel (20 g) by elution with 2% MeOH in CHCl$_3$. Crystallization of the product from 13% MeOH-CHCl$_3$ and EtOAc yielded the title compound as a yellow solid (19 mg, 15%): mp 297°–298° C.; $\nu_{max}$ 1740 (lactone), 1655 cm$^{-1}$ (pyridone); $^1$H NMR (TFA-d$_1$) δ1.05 (t, 3, J=7 Hz, H-18), 2.07 (q, 2, J=7 Hz, H-19), 5.60 (m, 2, H-17), 5.65 (s, 2, H-5), 7.89 (d, J=6 Hz, H-11), 8.05 (s, 1, H-14), 8.57 (d, J=6 Hz, H-10), 9.23 (s, 1, H-7). Anal. (C$_{18}$H$_{14}$N$_2$O$_4$S), calcd. C, 61.02; H, 3.95; N, 7.91. Found C, 60.65; H, 4.01; N, 7.78.

10,11-Methylenedioxy-20(RS)-camptothecin

The required ortho-aminoaldehyde was prepared by reduction of 2-nitropiperonal. This compound (60 mg, 0.36 mmol) and the tricyclic ketone 11 (53 mg, 0.20 mmol) were refluxed for 8 hr in toluene (30 mL) containing p-TsOH. H$_2$O (8 mg). The solvent was removed in vacuo, the red residue absorbed onto Celite (1 g) and chromatographed through silica gel (10 g) using 3% MeOH in CHCl$_3$. Concentration of the appropriate fractions gave 10.11-methylenedioxy-20(RS)-camptothecin (36 mg, 45%) as a pale tan solid. Crystallization of this material from CHCl₃ gave the analytical sample as a cream-colored solid: mp>250° C. (decomp); $v_{max}$ (KBr) 1750 (lactone), 1655 (pyridone), 1585 cm⁻¹ (aromatic); ¹H NMR (TFA-d₁) δ1.15 (t, 3, J=7 Hz, H-18), 2.16 (q, 2, J=7 Hz, H-19), 5.76 (ABq, 2, J=17 Hz, Δγ=85 Hz, H-17), 5.73 (s, 2, H-5), 6.44 (s, 2, OCH₂O), 7.55 (s, 1, H-14), 7.69 (s, 1, H-9), 8.16 (s, 1, H-12), 9.05 (s, 1, H-7). Anal. calcd for C₂₁H₁₆N₂O₆: 392.1008. Found 392.1009 (C₂₁H₁₆N₂O₆. 1.0 H₂O).

Preparation Of Water Soluble Camptothecin Analogs

The following non-limiting examples of water soluble camptothecin analogs were prepared as follows. The 9-glycinamido, 9-succinamido, 9-(N-methyl-piperazinocarbonylamino), 9-(N,N-diethylaminoethoxy carbonylamino), and 9-diethylaminoethoxy camptothecin analogs have the structures shown below.

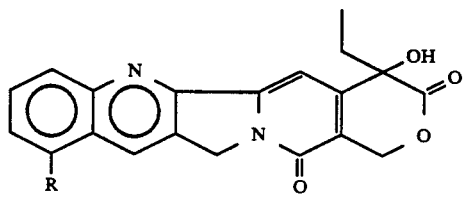

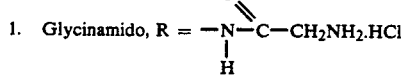

1. Glycinamido, R = —N—C—CH₂NH₂·HCl

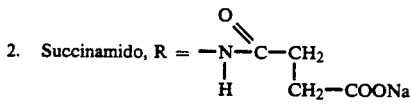

2. Succinamido, R = —N—C—CH₂
                     |   |
                     H   CH₂—COONa 3. N-Methylpiperazinocarbonylamino,

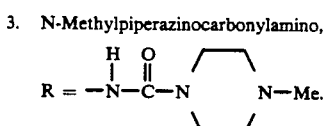

R = —N—C—N        N—Me·HCl

4. N,N-Diethylaminoethoxycarbonylamino,

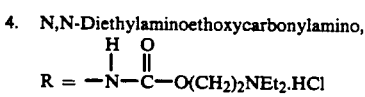

R = —N—C—O(CH₂)₂NEt₂·HCl

5. Diethylaminoethoxy,
   R = —O—(CH₂)₂NEt₂·HCl

Synthesis of 9-Glycinamido-20(RS)-camptothecin Hydrochloride

9-Amino-20(RA)-camptothecin was prepared from 2-amino-6-nitrobenzaldehyde and tricyclic ketone 11 by the process described above. 9-(tert-Butoxycarbonyl-glycinamido)-20(RS)-camptothecin.

A stirred solution of 9-amino-20(RS)-camptothecin (88 mg, 0.242 mmol) and N-(tert-butoxycarbonyl) glycine (110 mg, 0.629 mmol) in dry N,N-dimethylformamide (10 ml) under nitrogen was treated with dicyclohexylcarbonimide (125 mg, 0.607 mmol) at room temperature. After stirring for 18 hr., the turbid white mixture was filtered to remove the dicyclohexylurea byproduct. The solvent was removed by high vacuum distillation, and the tan-yellow residue was chromatographed through silica gel (25 g) using a stepwise gradient of 250 ml each of chloroform, 1% methanol/chloroform, and 2% methanol/chloroform. The appropriate fractions afforded 55 mg (44%) of the 9-tert-butoxycarboxyl glycinamido compound as a yellow solid. Recrystallization from methanol provided the sample as a beige solid, mp 208°-210° C. $v_{max}$ (KBr) 3360 (br, OH, amide NH), 1750 (lactone), 1710 (carbamate), 1692 (amide), 1660 (lactone), 1622, 1598, 1493, 1370, 1256, 1235, 1165, 1110, 1058, 1032, 825 and 728 cm⁻¹; ¹H NMR (DMSO-d₆) δ0.89 (t, 3, J=7 Hz, H-18), 1.44 (s, 9, C(CH₃)₃), 1.88 (m, 2, H-19), 3.92 (d, 2, J=6 Hz, COCH₂N), 5.29 (s, 2, H-5), 5.44 (s, 2, H-17), 6.53 (s, 1, OH), 7.19 (t, 1, J=6 Hz, CH₂NHCO), 7.37 (s, 1, H-14), 7.79 (d, 1, J=7 Hz, H-10), 7.85 (t, 1, J=7 Hz, H-11), 8.03 (d, 1, J=7 Hz, H-12), 8.79 (s, 1, H-7), and 10.20 (s, 1, amide H). Anal. calcd. for C₂₇H₂₈N₄O₇·H₂O: C, 60.21; H, 5.61; N, 10.40. Found: C, 60.35; H, 5.64; N, 10.23.

9-Glycinamido-20(RS)-camptothecin Hydrochloride

The tert-butoxycarboxylglycinamide derivative from above (21 mg, 0.040 mmol) was suspended in methylene chloride (10 ml) under nitrogen and then dissolved by the addition of methanol (0.75 ml). The stirred solution was chilled to 0° C. and treated over 5 min with a saturated solution of hydrogen chloride in anhydrous dioxane (4.5 ml) resulting in a turbid yellow solution. The stirred mixture was left to warm to room temperature, and after 2 hr. the solvents were removed under reduced pressured to give the deprotected compound as an orange-yellow solid (18 mg). The sample was taken up in deionized water (5 ml) and the hazy yellow solution filtered through a 0.45 μm membrane filter to remove extraneous water-insoluble material. The clear filtrate was lyophilized to provide the pure salt as a fluffy yellow solid (14 mg, 77%), mp darkening above 245° C. with no melting up to 310° C. $v_{max}$ (KBr) 2400–3650 cm⁻¹ (OH, amide H, amine HCl salt), 1742 (lactone), 1700 (amide, 1658 (pyridone), 1590, 1550, 1495, 1234, 1163, 1110, 1050, 902 820 and 720 cm⁻¹; ¹H NMR (DMSO-d₆) δ0.89 (t, J=7.5 Hz, H-18), 1.89 (m, 2, H-19), 4.03 (d, 2, J=5.4 Hz, COCH₂N), 5.30 (s, 2, H-5), 5.44 (s, 2, H-17), 7.37 (s, 1, H-14), 7.86 (d, 1, J=7 Hz, H-12), 7.92 (t, 1, J=7 Hz, H-11), 8.07 (d, 1, J=7 Hz, H-10), 8.35 (br S, 3, NH₃⁺), 8.95 (s, 1, H-7, 10.88 (s, 1, amide H). Anal. calcd. for C₂₂H₂₁ClN₄O₅·3H₂O: C, 51.71; H, 5.32; Cl, 6.94; N, 10.96. Found: C, 51.82; H, 5.23; Cl, 6.75; N, 10.61.

Synthesis of 9-Succinamido-20(RS)-camptothecin, Sodium Salt

The 9-succinamido derivative is synthesized from 9-amino-20(RS)-camptothecin (synthesis described above) by the following method.

9-Succinamido-20(RS)-camptothecin

A stirred suspension of 9-amino-20(RS)-camptothecin (400 mg, 1,102 mmol) and succinic anhydride (125 mg, 1.25 mmol) in pyridine (5 ml) under nitrogen was heated at 95° C. for 2 hr. The solvent was removed from the brown solution by high vacuum distillation to give the crude amide as a brown gum. Purification was effected by chromatography through silica gel employing a solvent gradient from 5% methanol/chloroform to 50% methanol/chloroform. Evaporation of the appropriate fractions gave 272 mg of the 9-succinamido compound as an orange-tan solid (53%), and recrystallization from methanol gave the material as a light tan solid, mg 265°-270° C. (decomp). $v_{max}$ (KBr) 2600–3650 (OH, NH, acid), 1738 (lactone), 1650 (pyridone), 1520–1610

(broad), 1485, 1400, 1232, 1160, 1110, 1050, 818, 720 cm$^{-1}$; $^1$H NMR (DMSO-d$_6$) δ0.89 (t, 3, J=7 Hz, H-18), 1.88 (m, 2, H-19), 2.45-2.50 (m, 4, —NCOCH$_2$CH$_2$CO$_2$H), 5.24 (s, 2, H-5), 5.42 (s, 2, H-17), 6.53 (br s, $\overline{1}$, OH), 7.33 (s, 1, H-14), 7.77 (t, 1, J=7 Hz, H-11), 7.85 (d, 1, J=7 Hz, H-12), 7.91 (d, 1, J=7 Hz, H-10), 8.83 (s, 1, H-7), 10.73 (br s, 1, amide $\underline{H}$ or CO$_2\underline{H}$). Calcd. for (M$^+$—CO$_2$—H$_2$O): 401.1375. Found: 401:1368. Calcd. for C$_{24}$H$_{21}$N$_3$O$_7$.2.5H$_2$O: C, 56.68; H, 4.73; N, 8.45. Found: C, 56.69; H, 4.65; N, 8.26.

Alternatively, the 9-succinamido derivative can be prepared by hydrolysis of its ethyl ester which is prepared by the following general method:

9-Amino-20(RS)-camptothecin in dry N,N-dimethylformamide containing pyridine is reacted at 0°-10° C. with a slight excess of ethylsuccinyl chloride in N,N-dimethylformamide solution. After work-up and chromatography on silica gel, a 75% yield of the 9-(ethyl)-glycinamide derivative is obtained.

9-Succinamido-20(RS)-camptothecin, Sodium Salt

The preceding succinamide free acid (151 mg, 0.326 mmol) was suspended in methanol (5 ml) and the stirred mixture treated dropwise at room temperature over 5 min with 0.1N aqueous sodium hydroxide solution (3.26 ml, 0.326 mmol, 1 eq.). During the addition the solution became hazy yellow-orange, and at the end of the addition the pH was near 7. The methanol was evaporated under reduced pressure, and the resulting aqueous solution was diluted with deionized water (6 ml). Filtration through a 0.5 μm membrane filter followed by lyophilization to provide the 9-succinamido-20(RS)-camptothecin salt as a fluffy orange-yellow solid (145 mg, 92%), mp >200° C. (decomp). $^1$H NMR (DMSO-d$_6$); δ0.89 (t, 3, J=7 Hz, H-18), 1.88 (m, 2, H-19), 2.41-2.60 (m, 4, —NCOCH$_2$CH$_2$CO$_2$Na), 5.30 (s, 2, H-5), 5.43 (s, 2, H-17), 6.55 (br s, 1, O$\underline{H}$), 7.33 (s, 1, H-14), 7.76 (t, 1, J=8 Hz, H-11), 7.87 ($\overline{d}$, 1, J=8 Hz, H-12), 8.16 (d, 1, J=8 Hz, H-10), 12.51 (br s, 1, amide $\underline{H}$).

Synthesis of 9-Diethylaminoethoxy-20(RS)-camptothecin Hydrochloride

The title compound is prepared from 9-hydroxy-20(RS)-camptothecin (synthesis of hydroxy-camptothecins described on pp. 30-32 of current Patent Application) in the following manner:

9-Diethylaminoethoxy-20(RS)-camptothecin

A stirred mixture of 9-hydroxy-20(RS)-camptothecin (20 mg, 0.055 mmol), N,N-diethylaminoethylchloride hydrochloride (15.4 mg, 0.090 mmol), and powdered anhydrous potassium carbonate (38 mg, 0.276 mmol) in anhydrous dimethylformamide (0.5 ml) was heated under nitrogen at 55° C. for 3 h. During the reaction, the mixture became clear yellow-orange and then tan. The solvent was removed by high vacuum distillation, and the tan residue was dispersed on Celite and chromatographed through silica gel (5 g) using 10% methanol/chloroform. Evaporation of the appropriate fractions gave 14 mg (55%) of the desired aminoether as a pale yellow solid. Recrystallization from ethyl acetate afforded the pure title compound as a beige solid, mp 173°-176° C. (decomp) γ$_{max}$(KBr) 3150-3650 (br, OH), 2967 and 2920 (CH), 1745 (lactone), 1658 (pyridone), 1592-1620 (aromatic), 1469, 1460, 1384, 1370, 1267, 1232, 1190, 1157, 1110, 1050, 810 and 720 cm$^{-1}$; $^1$H NMR (DMSO-d$_6$) δ0.89 (t, 3, J=7 Hz, H-18), 1.11 (t, 6, J=7 Hz, —N(CH$_2$CH$_3$)$_2$), 1.89 (m, 2, H-19), 2.82 (br s, 4, —N(CH$_2$CH$_3$)$_2$; with D$_2$O exchange, signal is at 2.88δ as a quartet, J=7 Hz), 3.17 (br s, 2, —OCH$_2$CH$_2$NEt$_2$; with D$_2$O exchange, signal is at 3.24δ as a fine triplet), 4.37 (m, 2, —OCH$_2$CH$_2$NEt$_2$), 5.29 (s, 2, H-5), 5.43 (s, 2, H-17), 6.53 (s, $\overline{1}$, 20-OH), 7.19 (d, 1, J=7 Hz, H-10), 7.33 (s, 1, H-14), 7.76 (m, $\overline{2}$, H-11 and H-12), 8.87 (s, 1, H-7). Anal. calcd. for C$_{26}$H$_{29}$N$_3$O$_5$: 463.2107; found: 463.2119. Calcd. for C$_{26}$H$_{29}$N$_3$O$_5$.2.0 H$_2$O: C, 62.52; H, 6.65; N, 8.41; found: C, 62.40; H, 6.75, N, 8.62.

Alternatively, similar yields of the title compound can be realized by reaction in refluxing acetone containing a catalytic amount of sodium iodide.

9-Diethylaminoethoxy-20(RS)-camptothecin Hydrochloride

The free base aminoether prepared as described above (275 mg) was suspended in methanol (4 ml) at room temperature and treated dropwise with 0.1N aqueous hydrochloric acid until pH 3 was achieved. The hazy orange solution was evaporated in a nitrogen stream, redissolved in deionized water (50 ml) and filtered through a 0.45 μm membrane. The clear yellow solution was frozen and lyophilized to afford the title compound as a bright yellow fluffy solid (273 mg), mp 232°-235° C. γ$_{max}$ (KBr) 2400-3650 (br irregular, OH, amine HCl salt, CH), 1745 (lactone), 1658 (pyridone), 1592 and 1620 (aromatic), 1465, 1400, 1370, 1266, 1232, 1193, 1014, 811 and 720 cm$^{-1}$; $^1$H NMR (DMSO-d$_6$) δ0.89 (t, 3, J=7 Hz, H-18), 1.33 (t, 6, J=7 Hz, —N(CH$_2$CH$_3$)$_2$), 1.88 (m, 2, H-19), 3.34 (m, 4, —N(CH$_2$C$\overline{H}$$_3$)$_2$, 3.63 fine t, 2—NCH$_2$CH$_2$O—), 4.63 (fine t,$\overline{2}$, Et$_2$NCH$_2$CH$_2$O—), 5.28 (s, $\overline{2}$, H-5), 5.53 (s, 2, H-17), 7.22 (m, 1, H-$\overline{10}$), 7.33 (s, 1, H-14), 7.79 (m, 2, H-11 and H-12), 9.05 (s, 1, H-7), 10.46 (br s, 1, ≡N⊕H). Anal. calcd. for C$_{26}$H$_{30}$ClN$_3$O$_5$.1.5 H$_2$O: C, 59.26; $\overline{H}$, 6.31; N, 7.97; Cl, 6.73. Found: C 59.48; H, 6.27; N, 7.81; Cl, 7.06.

Synthesis of 9-(4-methylpiperazino)carbonylamino-20(RS)-camptothecin Hydrochloride The title compound was prepared from 9-amino-20(RS)-camptothecin (synthesis of the amino-camptothecins is described on pp. 33 and 34 of current patent application) in the following manner:

9-(4-Methylpiperazino)carbonylamino-20(RS)-camptothecin.

The 9-amino-20(RS)-camptothecin was added to chloroform (treated with alumina to remove hydroxylic components) containing triethylamine. The resulting solution was treated with phosgene gas and filtered to remove solids. The filtrate containing the intermediate carbamoyl chloride was treated with N-methylpiperazine under nitrogen and left overnight. The turbid mixture was washed several times with aqueous sodium bicarbonate solution, dried and evaporated to afford the crude title compound. Chromatography on silica gel provided 9-(4-methylpiperazino)carbonylamino-20(RS)-camptothecin.

9-(4-Methylpiperazino)carbonylamino-20(RS)-camptothecin Hydrochloride

The preceding free base urea was suspended in methanol and treated with one equivalent of dilute aqueous hydrochloric acid. The methanol was evaporated and the aqueous residue filtered through a membrane filter.

The sample was lyophilized to provide the title compound.

Synthesis of 9-(N,N-Diethylaminoethoxy) carbonylamino-20(RS)-camptothecin Hydrochloride The title compound was prepared from 9-amino-20(RS)-camptothecin in the following manner:

9-(N,N-Diethylaminoethoxy) carbonylamino-20(RS)-camptothecin

The intermediate 9-carbamoyl chloride was prepared as in the preceding example. The resulting chloroform solution was treated with N,N-diethylaminoethanol under nitrogen. After standing overnight, the mixture was washed with aqueous sodium bicarbonate solution, dried and evaporated to afford the crude carbamate. Purification by silica gel chromatography gave the pure title carbamate as the free base.

9-(N,N-Diethylaminoethoxy)carbonylamino-20(RS)-camptothecin Hydrochloride

The free base from the preceding example was suspended in methanol and treated with one equivalent of dilute aqueous hydrochloric acid. The methanol was evaporated and the aqueous solution filtered (membrane). Lyophilization afforded the water soluble title carbamate.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A pharmaceutical composition comprising a camptothecin having the structure shown below

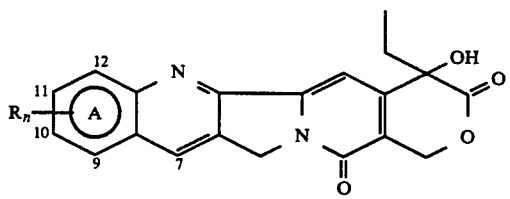

wherein $R_n$ is (a) an amino acid amido group obtained by reaction of an amino group at the 9, 10, 11 or 12-position of the A-ring with the carboxylic acid group of a naturally occurring α-amino acid, (b) a $C_{4-10}$ carboxylic acid amido group, (c) a urea group obtained by reaction of an amino group at the 9, 10, 11 or 12-position of the A-ring with phosgene followed by reaction with a diamine, (d) a urethane group obtained by reaction of an amino group at the 9, 10, 11 or 12-position of the A-ring with phosgene followed by reaction with a tertiary-amino alcohol, or a pharmaceutically acceptable salt thereof, and a pharmaceutically acceptable carrier.

2. The composition of claim 1, wherein said amino acid amido group is obtained by reaction of an amino group at the 9, 10, 11 or 12-position of the A-ring with the carboxylic acid group of a naturally occurring α-amino acid.

3. The composition of claim 2, wherein said amino acid amido group is the glycinamido group.

4. The composition of claim 1, wherein said carboxylic acid amido group is the succinamido group.

5. The composition of claim 1, wherein said urea group is obtained by reaction of an amino group at the 9, 10, 11 or 12-position of the A-ring with phosgene followed by a reaction with a diamine.

6. The composition of claim 1, wherein said urea group is the N-methylpiperazinocarbonylamino group.

7. The composition of claim 1, wherein said urethane group is obtained by reaction of an amino group at the 9, 10, 11 or 12-position of the A-ring with phosgene followed by a reaction with a tertiary-amino alcohol.

8. The composition of claim 1, wherein said urethane group is the N,N-diethylaminoethoxycarbonylamino group.

9. A method of inhibiting the activity of the enzyme topoisomerase I by contacting said enzyme with a camptothecin having the structure shown below

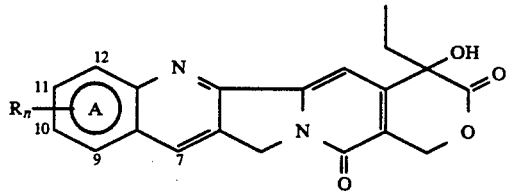

wherein $R_n$ is (a) an amino acid amido group obtained by reaction of an amino group at the 9, 10, 11 or 12-position of the A-ring with the carboxylic acid group of a naturally occurring α-amino acid, (b) a $C_{4-10}$ carboxylic acid amido group, (c) a urea group obtained by reaction of an amino group at the 9, 10, 11 or 12-position of the A-ring with phosgene followed by reaction with a diamine, (d) a urethane group obtained by reaction of an amino group at the 9, 10, 11 or 12-position of the A-ring with phosgene followed by reaction with a tertiaryamino alcohol, or a pharmaceutically acceptable salt thereof.

10. The method of claim 9, wherein $R_n$ is an amino acid amido group.

11. The method of claim 9, wherein $R_n$ is a $C_{4-10}$ carboxylic acid amido group.

12. The method of claim 9, wherein $R_n$ is a urea group.

13. The method of claim 9, wherein $R_n$ is a urethane group.

* * * * *